US010590099B1

(12) United States Patent
Sookraj

(10) Patent No.: US 10,590,099 B1
(45) Date of Patent: Mar. 17, 2020

(54) PROCESSES FOR PRODUCING BETA-LACTONE WITH HETEROGENOUS CATALYSTS

(71) Applicant: Novomer, Inc., Waltham, MA (US)

(72) Inventor: Sadesh H. Sookraj, Cambridge, MA (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/674,453

(22) Filed: Aug. 10, 2017

(51) Int. Cl.
| | |
|---|---|
| *C07D 305/12* | (2006.01) |
| *C07D 305/14* | (2006.01) |
| *C07D 407/12* | (2006.01) |
| *C07D 407/06* | (2006.01) |
| *B01J 31/18* | (2006.01) |
| *B01J 37/08* | (2006.01) |
| *B01J 31/20* | (2006.01) |
| *B01J 37/04* | (2006.01) |
| *B01J 37/02* | (2006.01) |

(52) U.S. Cl.
CPC ........ *C07D 305/12* (2013.01); *B01J 31/1815* (2013.01); *B01J 31/20* (2013.01); *B01J 37/0201* (2013.01); *B01J 37/0236* (2013.01); *B01J 37/04* (2013.01); *B01J 37/08* (2013.01); *C07D 305/14* (2013.01); *C07D 407/06* (2013.01); *C07D 407/12* (2013.01); *B01J 2531/0213* (2013.01)

(58) Field of Classification Search
CPC .................................................. C07D 305/12
See application file for complete search history.

(56) References Cited

U.S. PATENT DOCUMENTS

| | | | |
|---|---|---|---|
| 3,885,155 A | 5/1975 | Anbar | |
| 4,427,884 A | 1/1984 | Anbar et al. | |
| 4,973,841 A | 11/1990 | Purser | |
| 5,256,828 A | 10/1993 | Cuscurida et al. | |
| 5,310,948 A | 5/1994 | Drent et al. | |
| 5,359,081 A | 10/1994 | Drent et al. | |
| 5,438,194 A | 8/1995 | Koudijs et al. | |
| 5,661,299 A | 8/1997 | Purser | |
| 6,852,865 B2 | 2/2005 | Coates et al. | |
| 7,420,064 B2 | 9/2008 | Luinstra et al. | |
| 8,445,703 B2 * | 5/2013 | Valente et al. ........ | C07D 305/12 549/328 |
| 8,796,475 B2 * | 8/2014 | Allen .................... | C07D 305/12 549/328 |
| 9,096,510 B2 | 8/2015 | Porcelli et al. | |
| 9,156,803 B2 | 10/2015 | Allen et al. | |
| 9,206,144 B2 | 12/2015 | Allen et al. | |
| 9,327,280 B2 | 5/2016 | Lee et al. | |
| 9,403,788 B2 | 8/2016 | Lee et al. | |
| 9,493,391 B2 | 11/2016 | Allen et al. | |
| 9,738,784 B2 | 8/2017 | Allen et al. | |
| 9,914,689 B2 | 3/2018 | Porcelli et al. | |
| 10,065,914 B1 | 9/2018 | Ruhl et al. | |
| 10,099,988 B2 | 10/2018 | Farmer et al. | |
| 10,099,989 B2 | 10/2018 | Sookraj | |
| 10,144,802 B2 | 12/2018 | Sookraj | |
| 10,221,150 B2 | 3/2019 | Farmer et al. | |
| 10,221,278 B2 | 3/2019 | Lee et al. | |
| 10,245,559 B2 | 4/2019 | Lapointe et al. | |
| 2005/0014977 A1 | 1/2005 | Drent et al. | |
| 2007/0161806 A1 | 7/2007 | Preishuber-Pflugl et al. | |
| 2012/0123137 A1 | 5/2012 | Allen et al. | |
| 2013/0165670 A1 | 6/2013 | Allen et al. | |
| 2013/0209775 A1 | 8/2013 | Allen et al. | |
| 2013/0281715 A1 | 10/2013 | Allen et al. | |
| 2014/0275575 A1 | 9/2014 | Allen et al. | |
| 2014/0296522 A1 | 10/2014 | Lee et al. | |
| 2014/0309399 A1 | 10/2014 | Porcelli et al. | |
| 2015/0005513 A1 | 1/2015 | Lee et al. | |

(Continued)

FOREIGN PATENT DOCUMENTS

| | | |
|---|---|---|
| WO | 2009/155086 A2 | 12/2009 |
| WO | WO 2010/118128 | 10/2010 |

(Continued)

OTHER PUBLICATIONS

Kegel, W., et al. "The Immobilization of a Transfer Hydrogenation Catalyst on Colloidal Particles." ChemCatChem. (2017), vol. 9, pp. 440-450. (Year: 2017).*
Church, et al., Carbonylation of Heterocycles by Homogeneous Catalysts, Chem. Commun., Jan. 19, 2007 (5 pages), Royal Society of Chemistry 2018.
Inoue, et al., "Organometallic-Catalyzed Polymerization of Propiolactone" Makromol. (1961), Chem., 48: 229-233 https://doi.org/10.1002/macp.1961.020480121.

*Primary Examiner* — Andrew D Kosar
*Assistant Examiner* — John S Kenyon
(74) *Attorney, Agent, or Firm* — Young Basile Hanlon & MacFarlane, P.C.

(57) ABSTRACT

The present invention is directed to processes from producing beta-lactone and beta-lactone derivatives using heterogenous catalysts. In preferred embodiments of the present invention, the processes comprise the steps: passing a feed stream comprising an epoxide reagent and a carbon monoxide reagent to a reaction zone; contacting the epoxide reagent and the carbon monoxide reagent with a heterogenous catalyst to produce a beta-lactone product in the reaction zone; and removing the beta-lactone product from the reaction zone. In preferred embodiments, the heterogenous catalyst comprises a solid support containing a cationic Lewis acid functional group and a metal carbonyl compound comprising at least one of anionic metal carbonyl compound or a neutral metal carbonyl compound. In certain preferred embodiments, the epoxide reagent and carbon monoxide reagent have a biobased content.

19 Claims, No Drawings

(56) References Cited

U.S. PATENT DOCUMENTS

| | | |
|---|---|---|
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0002400 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | | |
|---|---|---|---|
| WO | WO-2010118128 A1 * | 10/2010 | ........... C07D 305/12 |
| WO | 2012/030619 A1 | 3/2012 | |
| WO | 2012/051219 A2 | 4/2012 | |
| WO | 2012/158573 A1 | 11/2012 | |
| WO | WO 2013/063191 | 5/2013 | |
| WO | 2013/122905 A1 | 8/2013 | |
| WO | 2013/126375 A1 | 8/2013 | |
| WO | 2014/004858 A1 | 1/2014 | |
| WO | 2014/008232 A2 | 1/2014 | |
| WO | 2015/085295 A2 | 6/2015 | |
| WO | 2015/138975 A1 | 9/2015 | |
| WO | 2015/171372 A1 | 11/2015 | |
| WO | 2015/184289 A1 | 12/2015 | |
| WO | 2016/015019 A1 | 1/2016 | |
| WO | 2016/130947 A1 | 8/2016 | |
| WO | 2016/130977 A1 | 8/2016 | |
| WO | 2016/130988 A1 | 8/2016 | |
| WO | 2016/130993 A1 | 8/2016 | |
| WO | 2016/130998 A1 | 8/2016 | |
| WO | 2016/131001 A1 | 8/2016 | |
| WO | 2016/131003 A1 | 8/2016 | |
| WO | 2016/131004 A1 | 8/2016 | |
| WO | 2017/023777 A1 | 2/2017 | |
| WO | 2017/023820 A1 | 2/2017 | |
| WO | 2017/165323 A1 | 9/2017 | |
| WO | 2017/165344 A1 | 9/2017 | |
| WO | 2017/165345 A1 | 9/2017 | |
| WO | 2018/085251 A1 | 5/2018 | |
| WO | 2018/085254 A1 | 5/2018 | |
| WO | 2018/106824 A1 | 6/2018 | |
| WO | 2018/107185 A1 | 6/2018 | |
| WO | 2018/136638 A1 | 7/2018 | |
| WO | 2018/144998 A1 | 8/2018 | |
| WO | 2018/170006 A1 | 9/2018 | |
| WO | 2018/200466 A1 | 11/2018 | |
| WO | 2018/200471 A1 | 11/2018 | |
| WO | 2019/006366 A1 | 1/2019 | |
| WO | 2019/006377 A1 | 1/2019 | |
| WO | 2019/050649 A1 | 3/2019 | |
| WO | 2019/051184 A1 | 3/2019 | |
| WO | 2019/070981 A1 | 4/2019 | |

* cited by examiner

PROCESSES FOR PRODUCING BETA-LACTONE WITH HETEROGENOUS CATALYSTS

FIELD OF THE INVENTION

This invention generally relates to processes for the improved production of beta-lactone and beta-lactone derivatives. Specifically, this invention relates to processes for carbonylation of epoxides with carbon monoxide using heterogenous catalysts. Advantageously, embodiments of the present invention may more efficiently produce beta-lactone and beta-lactone derivatives from various carbon sources including petroleum and biobased material.

BACKGROUND OF THE INVENTION

For the purposes of this invention, the terms "biobased", "biobased content", and "bio-content" are used interchangeably to describe carbon atoms from biological sources, recycled sources, renewable sources, and/or otherwise sustainable sources. Carbon atoms are fundamental building blocks for many manufactured materials. Introducing biobased carbons into manufactured materials may have positive environmental effects.

The term "carbonylation" generally refers to chemical reactions that introduce carbon monoxide molecules into other organic and inorganic substrate molecules. Carbonylation results in a substrate molecule gaining a carbonyl functional group. Carbonylation reactions are important in industrial chemistry and are becoming a more important building block for fine and bulk chemicals. Conventional processes use homogenous catalysts for the carbonylation of epoxides to produce beta-lactones similar to the following reaction:

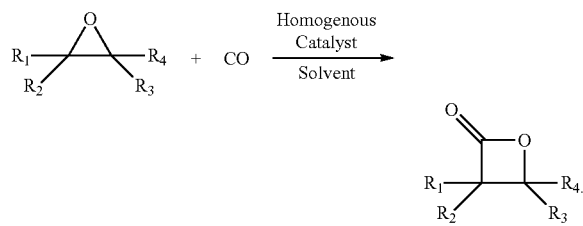

A catalyst comprises one or more atoms which may alter the rate chemical reactions and/or provide an alternative mechanism for a chemical reaction with a different transition state and/or activation energy. A homogenous catalyst, includes an atom, ion, or molecule with a particular function that is in the same phase as the reagents of a chemical reaction.

Conventional processes for carbonylation of epoxides to produce beta-lactones using homogenous catalysts may have costs associated with catalysts recycle and material recovery that could be reduced or eliminated using heterogenous catalyst systems. Certain conventional processes require the use of homogenous catalyst in a solvent. In order to reuse the catalyst, the catalyst in solvent must be passed through expensive membranes to recycle the catalyst. Conventional homogenous processes may involve the use of large volumes of solvent, hence requiring larger capacity reactors which result in higher costs associated with the size of the reactors and higher costs associated with moving large volumes of solvent through the system. Also, the processes including solvent usually require distillation resulting in extra costs associated with heating and distillation equipment.

There is a need for less costly and more efficient processes for producing beta-lactones and beta-lactone derivatives by carbonylation of epoxides with carbon monoxide. The present invention satisfies this need with processes for carbonylation of epoxides with carbon monoxide using heterogenous catalysts.

SUMMARY OF THE INVENTION

The present invention is directed to processes for reacting the contents of a feed stream comprising an epoxide reagent and a carbon monoxide reagent with a heterogenous catalyst to produce a product stream comprising a beta-lactone product. Advantageously, the processes of the present invention have more efficient steps and eliminate certain costs associated with conventional processes for production of beta-lactones and beta-lactone derivatives.

One object of the present invention is to provide more efficient processes for production of beta-lactones and beta-lactone derivatives by reducing the utilities required to store, transfer, purify and heat solvents used in conventional processes.

Another object is to reduce the cost of materials associated with conventional processes by eliminating the need for filtration membranes, reducing or eliminating the amount of solvent used, and reducing the size of reactors necessary for production of beta-lactones and beta-lactone derivatives.

One advantage of the present invention provides for positive environmental with more efficient processes having smaller carbon footprints. Advantageously, embodiments of the present invention provide an improved life cycle assessment for beta-lactones and beta-lactone derivatives.

In preferred embodiments, the processes of the present invention overcome the deficiencies of conventional systems by providing for carbonylation of a broad range of epoxide reagents with carbon monoxide reagents to form a broad range of beta-lactones. In certain embodiments, the beta-lactones may be removed as products. In certain other embodiments, the beta-lactones may undergo further reactions to produce beta-lactone derivatives.

Preferred embodiments achieve the objects and advantages of the present invention through processes including carbonylation with a heterogenous catalyst comprising a cationic Lewis acid functional group and an anionic metal carbonyl. In certain preferred embodiments, the heterogenous catalyst comprises an organometallic compound such as a carbonyl cobaltate, a metal porphyrin compound, a metal salen compound, and/or a metal salophen compound. In certain preferred embodiments, the heterogenous catalyst may comprise a metal such as those from Groups 1 or 2 of the periodic table. In certain embodiments, the heterogenous catalyst may comprise a metal such as Ti, V, Cr, Mo, W, Mn, Tc, Re, Fe, Ru, Os, Co, Rh, Ir, Ni, or Al.

Specifically, preferred embodiments of the present invention include processes for carbonylation of epoxides with carbon monoxide using heterogenous catalysts. Embodiments of the present invention may efficiently produce beta-lactone and beta-lactone derivatives from various sources including refined petroleum sources, synthetic sources, and biobased sources.

While this disclosure is susceptible to various modifications and alternative forms, specific exemplary embodiments thereof have been shown by way of example and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

DETAILED DESCRIPTION OF EMBODIMENTS

Definitions

The terms bio-content and biobased content mean biogenic carbon also known as bio-mass derived carbon, carbon waste streams, and carbon from municipal solid waste. In some variations, bio-content (also referred to as "biobased content") can be determined based on the following:

Bio-content or Biobased content=[Bio (Organic) Carbon]/ [Total (Organic) Carbon] 100%, as determined by ASTM D6866 (Standard Test Methods for Determining the Biobased (biogenic) Content of Solid, Liquid, and Gaseous Samples Using Radiocarbon Analysis).

The bio-content of the beta-lactones produced may depend based on the bio-content of the epoxide reagent and carbon monoxide reagent. For example, in some variations of the processes described herein, the epoxide reagent and carbon monoxide reagent described herein may have a bio-content of greater than 0%, and less than 100%. In certain variations of the processes described herein, the epoxide reagent and carbon monoxide reagent described herein may have a bio-content of at least 10%, at least 30%, at least 50%, at least 70%, at least 95%, at least 99%, or 100%. In certain variations, epoxide reagent and carbon monoxide reagent derived from renewable sources may be used. In other variations, at least a portion of the epoxide reagent and/or carbon monoxide reagent is derived from renewable sources.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain at least one units of unsaturation, but which is not aromatic. Unless otherwise specified, aliphatic groups contain 1-30 carbon atoms. In some aspects, aliphatic groups contain 1-12 carbon atoms. In some aspects, aliphatic groups contain 1-8 carbon atoms. In some aspects, aliphatic groups contain 1-6 carbon atoms. In some aspects, aliphatic groups contain 1-5 carbon atoms, in some aspects, aliphatic groups contain 1-4 carbon atoms, in yet other aspects aliphatic groups contain 1-3 carbon atoms, and in yet other aspects, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl) alkyl or (cycloalkyl)alkenyl.

The term "heteroaliphatic," as used herein, refers to aliphatic groups wherein at least one carbon atoms are independently replaced by at least one atoms selected from the group consisting of oxygen, sulfur, nitrogen, phosphorus, or boron. In some aspects, one or two carbon atoms are independently replaced by at least one of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetitions of units derived, actually or conceptually, from molecules of low relative molecular mass. In some aspects, a polymer is comprised of only one monomer species. In some aspects, a polymer is a copolymer, terpolymer, heteropolymer, block copolymer, or tapered heteropolymer of at least one epoxides.

The term "unsaturated", as used herein, means that a moiety has at least one double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some aspects, the cycloalkyl has 3-6 carbons. Representative carbocyles include cyclopropane, cyclobutane, cyclopentane, cyclohexane, bicyclo[2,2,1]heptane, norbornene, phenyl, cyclohexene, naphthalene, and spiro[4.5]decane. The terms "cycloaliphatic", "carbocycle" or "carbocyclic" also include aliphatic rings that are fused to at least one aromatic or nonaromatic rings, such as decahydronaphthyl or tetrahydronaphthyl, where the radical or point of attachment is on the aliphatic ring. In some aspects, a carbocyclic group is bicyclic. In some aspects, a carbocyclic group is tricyclic. In some aspects, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In some aspects, alkyl groups contain 1-8 carbon atoms. In some aspects, alkyl groups contain 1-6 carbon atoms. In some aspects, alkyl groups contain 1-5 carbon atoms, in some aspects, alkyl groups contain 1-4 carbon atoms, in yet other aspects, alkyl groups contain 1-3 carbon atoms, and in yet other aspects alkyl groups contain 1-2 carbon atoms. Examples of alkyl radicals include, but are not limited to, methyl, ethyl, n-propyl, isopropyl, n-butyl, iso-butyl, secbutyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some aspects, "aryl" refers to an aromatic ring system which includes, but is not limited to, phenyl, naphthyl, anthracyl and the like, which may bear at least one substituents. Also included within the scope of the term "aryl", as it is used herein, is a group in which an aromatic ring is fused to at least one additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 □ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to at least one aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, at least one, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to at least one aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds may contain "optionally substituted" moieties. In general, the term "substituted", whether preceded by the term "optionally" or not, means that at least one hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned may include those that result in the formation of stable or chemically feasible compounds. The term "stable", as used herein, refers to compounds that are not substantially altered when subjected to conditions to allow for their production, detection, and, in some aspects, their recovery, purification, and use for at least one of the purposes disclosed herein.

In some chemical structures herein, substituents are shown attached to a bond which crosses a bond in a ring of the depicted molecule. This means that at least one of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R this has the same meaning as if the ring were said to be "optionally substituted" as described in the preceding paragraph.

As used herein, the term "catalyst" refers to a substance the presence of which increases the rate of a chemical reaction, while not being consumed or undergoing a permanent chemical change itself.

Renewable sources means a source of carbon and/or hydrogen obtained from biological life forms that can replenish itself in less than one hundred years.

Renewable carbon means carbon obtained from biological life forms that can replenish itself in less than one hundred years.

Recycled sources mean carbon and/or hydrogen recovered from a previous use in a manufactured article.

Recycled carbon means carbon recovered from a previous use in a manufactured article.

As used herein, the term "about" preceding at least one numerical values means the numerical value ±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

Exemplary Embodiments

In preferred embodiments of the present invention, the processes include a step for reacting the contents of a feed stream comprising an epoxide reagent and a carbon monoxide reagent with a heterogenous catalyst in a reaction zone to produce a product stream comprising a beta-lactone product. Preferably, the beta-lactone product may be removed from the reaction zone in a liquid phase or a gas phase. In preferred embodiments, the heterogenous catalyst is in a solid phase. Advantageously, the processes of the present invention do not require a membrane, filter, or sieve to remove the heterogenous catalyst from the beta-lactone product.

In certain preferred embodiments of the present invention, the processes comprise the steps: passing a feed stream comprising an epoxide reagent and a carbon monoxide reagent to a reaction zone; contacting the epoxide reagent and the carbon monoxide reagent with a heterogenous catalyst to produce a beta-lactone product in the reaction zone; and removing the beta-lactone product from the reaction zone. Preferably, the processes of the present invention do not require the use of solvent to dissolve reagents or products. Therefore, certain embodiments of the processes do not require a distillation step to separate the beta-lactone product from a solvent.

In certain other preferred embodiments, the processes comprise the steps: passing a feed stream comprising an epoxide reagent and a carbon monoxide reagent to a reaction zone; contacting the epoxide reagent and the carbon monoxide reagent with a heterogenous catalyst to produce a beta-lactone intermediate in the reaction zone; reacting the beta-lactone intermediate with a derivative reagent in the reaction zone to produce a beta-lactone derivative; and removing the beta-lactone derivative from the reaction zone. A derivative reagent may be chosen from a list including a carbon monoxide reagent, beta-lactone reagent, an ammonia reagent, an alcohol reagent. Preferably, the beta-lactone intermediate remains in the reactor and is reacted with the derivative reagent. Advantageously, the processes of the present invention do not require unnecessary steps for separation or isolation of intermediates.

Embodiments of the present invention configured for producing a beta-lactone derivative may include the insertion of a heteroatom such as by nucleophilic addition. Typical heteroatoms are nitrogen, oxygen, sulfur, phosphorus, chlorine, bromine, and iodine and includes any oxidized form of nitrogen or sulfur, and any quaternized form of a basic nitrogen. In certain preferred embodiments, the insertion of the heteroatom opens the beta-lactone ring and adds a hydroxyl group, hydroxyalkyl group, amine group, amide group, ester group, carbonyl group, carbonate group, carboxylic acid group, aldehyde group, keto group, ether group, and/or urethane group to name a few.

In still other preferred embodiments, the processes comprise the steps: passing a feed stream comprising an epoxide reagent and a carbon monoxide reagent to a reaction zone through a feed stream inlet; contacting the epoxide reagent and the carbon monoxide reagent with a heterogenous catalyst to produce a beta-lactone intermediate in the reactor; polymerizing the beta-lactone intermediate in the reactor to produce a polylactone product; removing the polylactone product from the reactor through a product stream outlet.

In certain embodiments, the processes of the present invention are performed with a reactor configured for a continuous operation and wherein the epoxide reagent and carbon monoxide reagent are continuously fed to a reaction zone of the reactor. In some embodiments, the reactor is mixed. In other embodiments, there is no mixing in the reactor. In some embodiments, the epoxide reagent and/or carbon monoxide reagent may be fed to the reactor at ambient temperature and pressure and then heated or pressurized to reaction conditions once in the reactor. In other embodiments, the epoxide reagent and/or carbon monoxide reagent may be fed to the reactor above ambient temperature and pressure. The reactor itself may be any reactor conducive to continuous operation, including but not limited to a fixed bed reactor, moving bed reactor, fluidized bed reactor, trickle bed reactor, catalytic distillation reactor, continuously stirred tank reactor, or a tubular reactor. In some embodiments, the reactor is an adiabatic reactor, and/or an isothermal reactor. In some embodiments, the reactor pressure is constant. In some embodiments, the reactor pressure varies as the reaction progresses. In some embodiments, the reactor temperature varies as the reaction progress. In some embodiments, the reaction is performed in a batch operation. One of ordinary skill in the art will recognize the temperatures, pressures, catalyst ratios, concentrations of reactants, and flow rates can all be optimized or varied to achieve a given reaction outcome.

In certain preferred embodiments, the processes of the present invention may include an epoxide reagent and carbon monoxide reagent introduced to a reactor in an amount sufficient for carbonylation under superatmospheric pressure. In certain embodiments, the epoxide reagent and/or carbon monoxide reagent is provided at a pressure in the range from about 50 psi (350 kPa) to about 5000 psi (35 MPa). In certain embodiments, the epoxide reagent and/or carbon monoxide reagent is more preferably provided at a pressure from about 200 psi (1.4 MPa) to about 600 psi (4.1 MPa).

In some embodiments, the processes of the present invention may introduce the epoxide reagent and/or carbon monoxide reagent at a weight hourly space velocity of 0.1 to 20 $hr^{-1}$, more typically 0.25 to 10 $hr^{-1}$, and preferably, 0.5 to 5 $hr^{-1}$. In some embodiments, the flow rate from the epoxide reagent and/or carbon monoxide reagent is set to about the stoichiometric value for a carbonylation reaction, to about 0.1% higher than the stoichiometric value, to about 1% higher than the stoichiometric value, to about 5% higher than the stoichiometric value, to about 10% higher than the stoichiometric value, to about 15% higher than the stoichiometric value, or to about 20% higher than the stoichiometric value. In certain preferred embodiments, the flow rate from the epoxide reagent is set to at least 0.1% higher than the stoichiometric value for a carbonylation reaction.

In some embodiments, the feed stream includes a Lewis base additive. In some embodiments, such Lewis base additives can stabilize or reduce deactivation of the heterogenous catalyst. In some embodiments, the Lewis base additive is a modified THF; 2,6-lutidine; imidazole, 1-methylimidazole 4-dimethylaminopyridine, trihexylamine and triphenylphosphine.

Within the reactor, the epoxide reagent and carbon monoxide reagent contact the heterogenous catalyst to produce at least one beta-lactone and/or beta-lactone derivative. The beta-lactones and beta-lactone derivatives that can be produced from epoxide reagents and/or carbon monoxide reagents may have a bio-content of at least 10% and preferably at least at least 30%, at least 50%, at least 70%, at least 90%, at least 95%, at least 99%, or 100%. Table 1 illustrated below includes Column A directed to a non-exhaustive list of epoxides which may undergo carbonylation to produce beta-lactone according to the processes of the present invention and Column B directed to a non-exhaustive list of beta-lactones which may be produced according to the present invention.

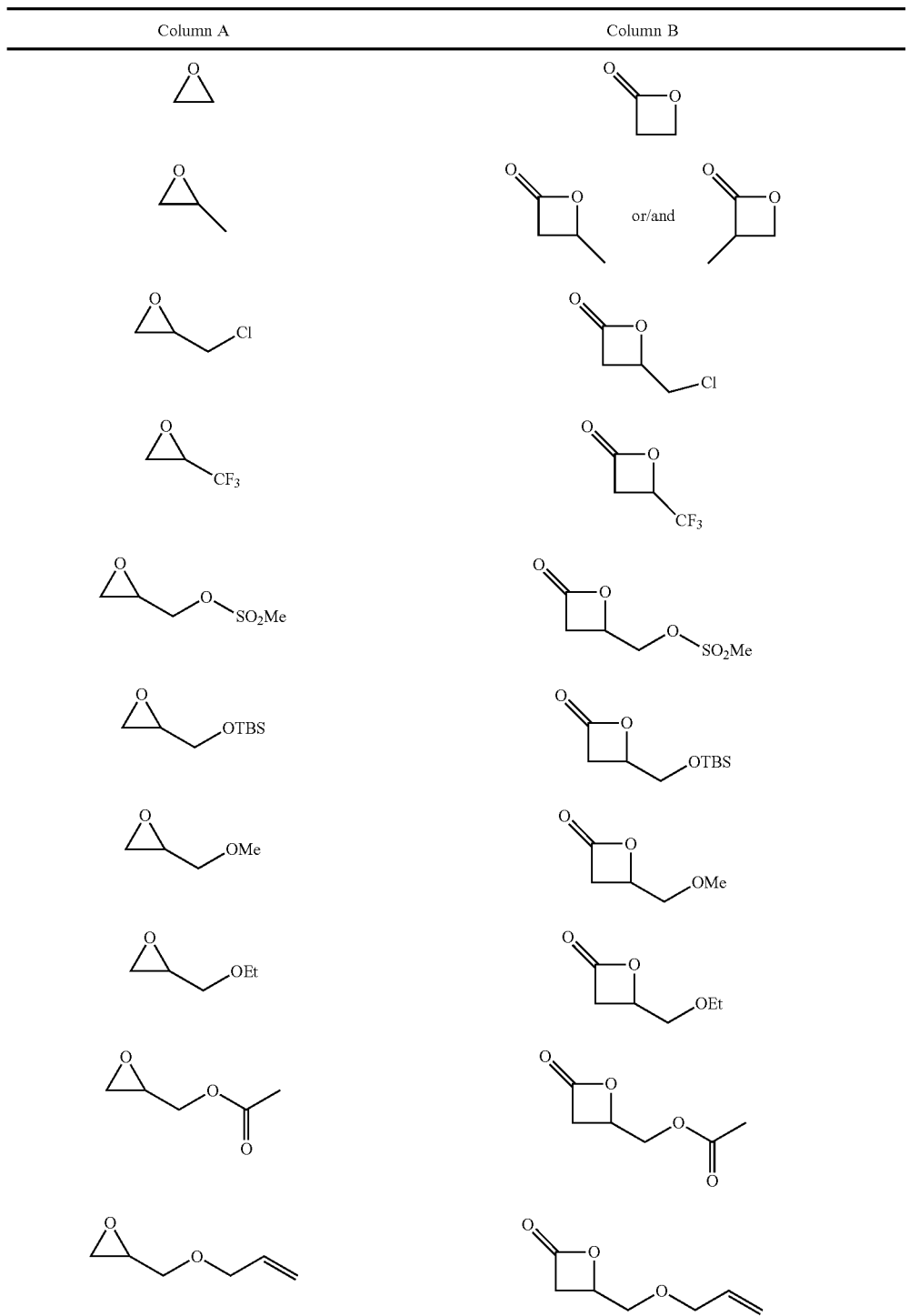

-continued
| Column A | Column B |
|---|---|
| 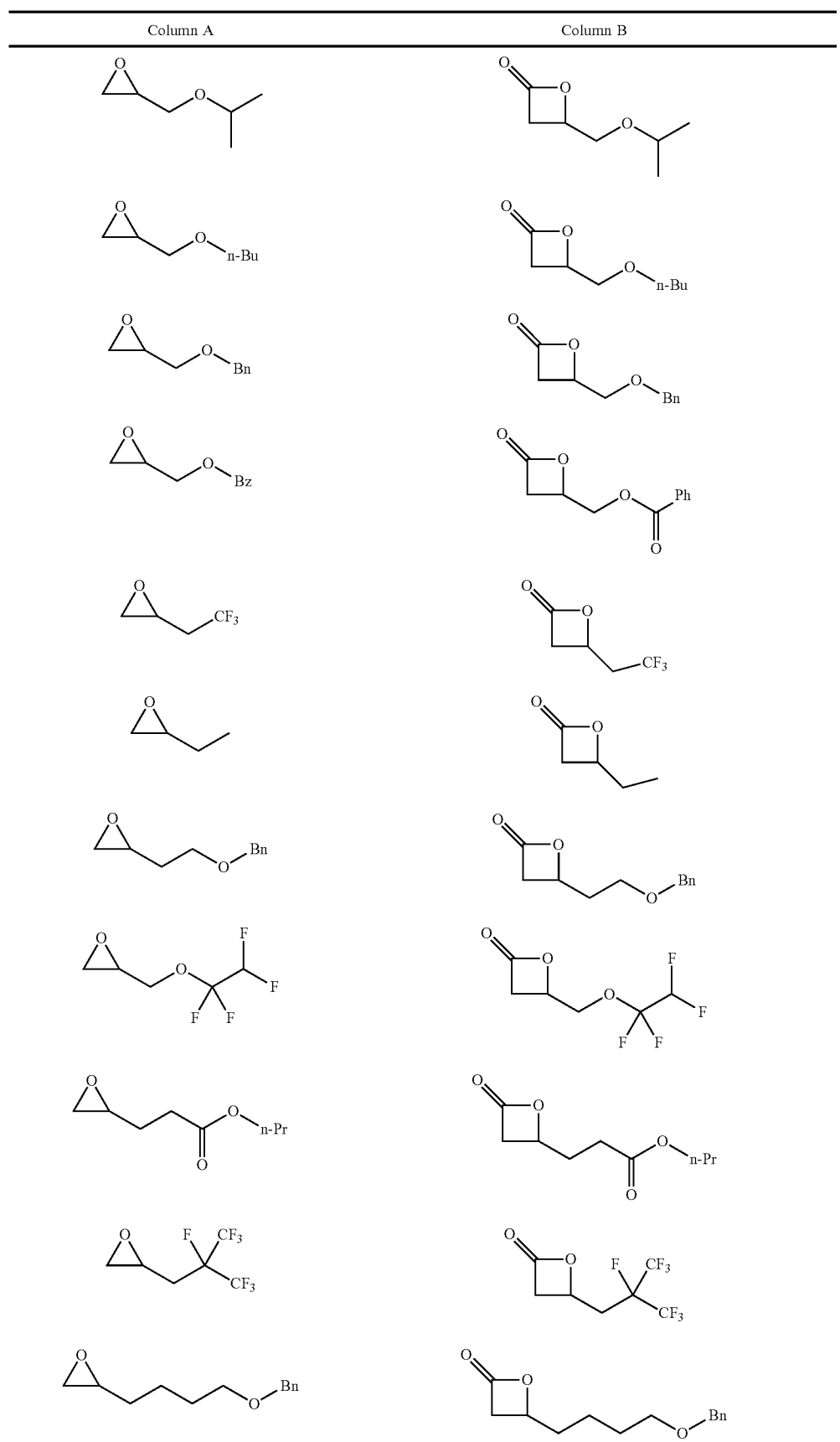 | |

-continued
| Column A | Column B |
| --- | --- |
| 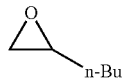 | 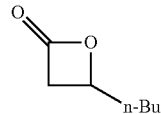 |
| 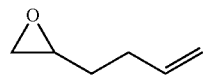 | 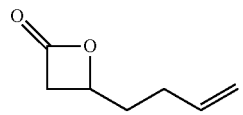 |
| 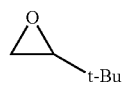 | 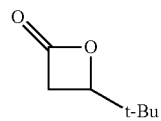 |
| 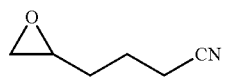 | 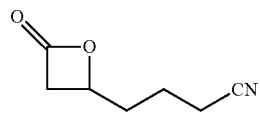 |
| 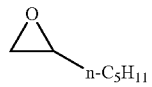 | 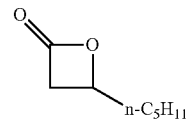 |
| 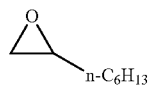 | 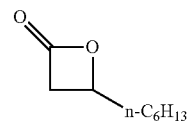 |
| 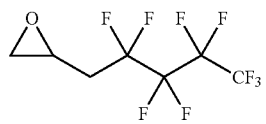 [SMILES: FC(F)(F)C(F)(F)C(F)(F)C(F)(F)CC1CO1] | 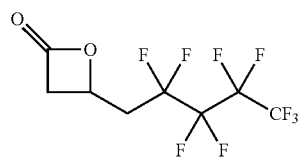 [SMILES: O=C1CC(CC(F)(F)C(F)(F)C(F)(F)C(F)(F)F)O1] |
| 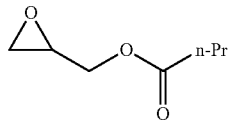 | 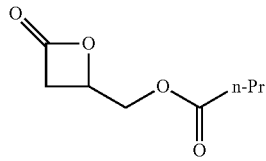 |
| 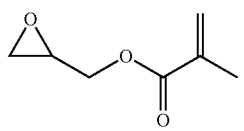 | 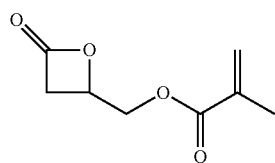 |
| 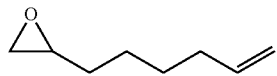 | 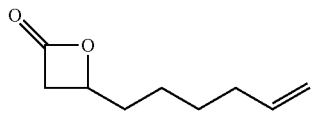 |

-continued
| Column A | Column B |
| --- | --- |
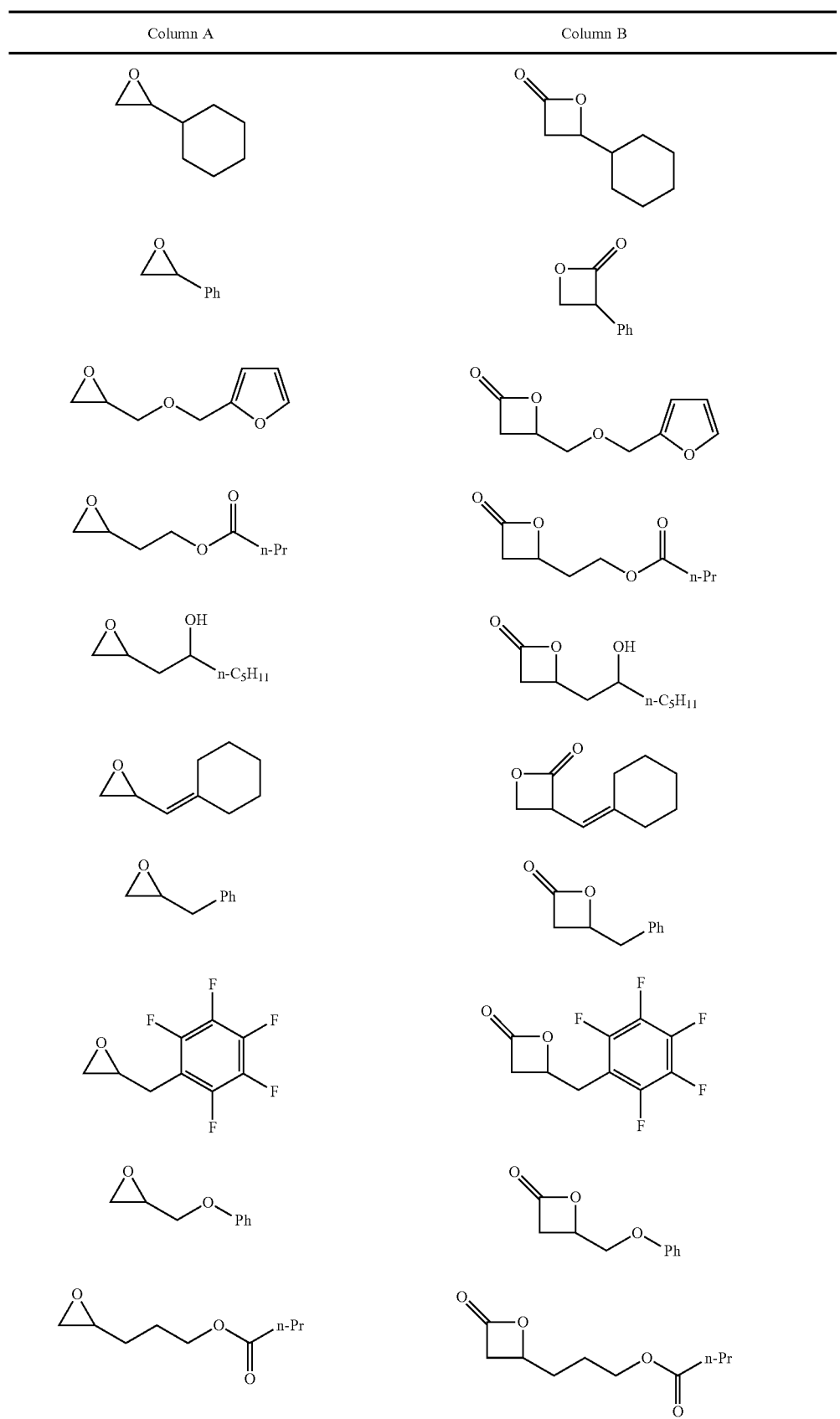

-continued
| Column A | Column B |
|---|---|
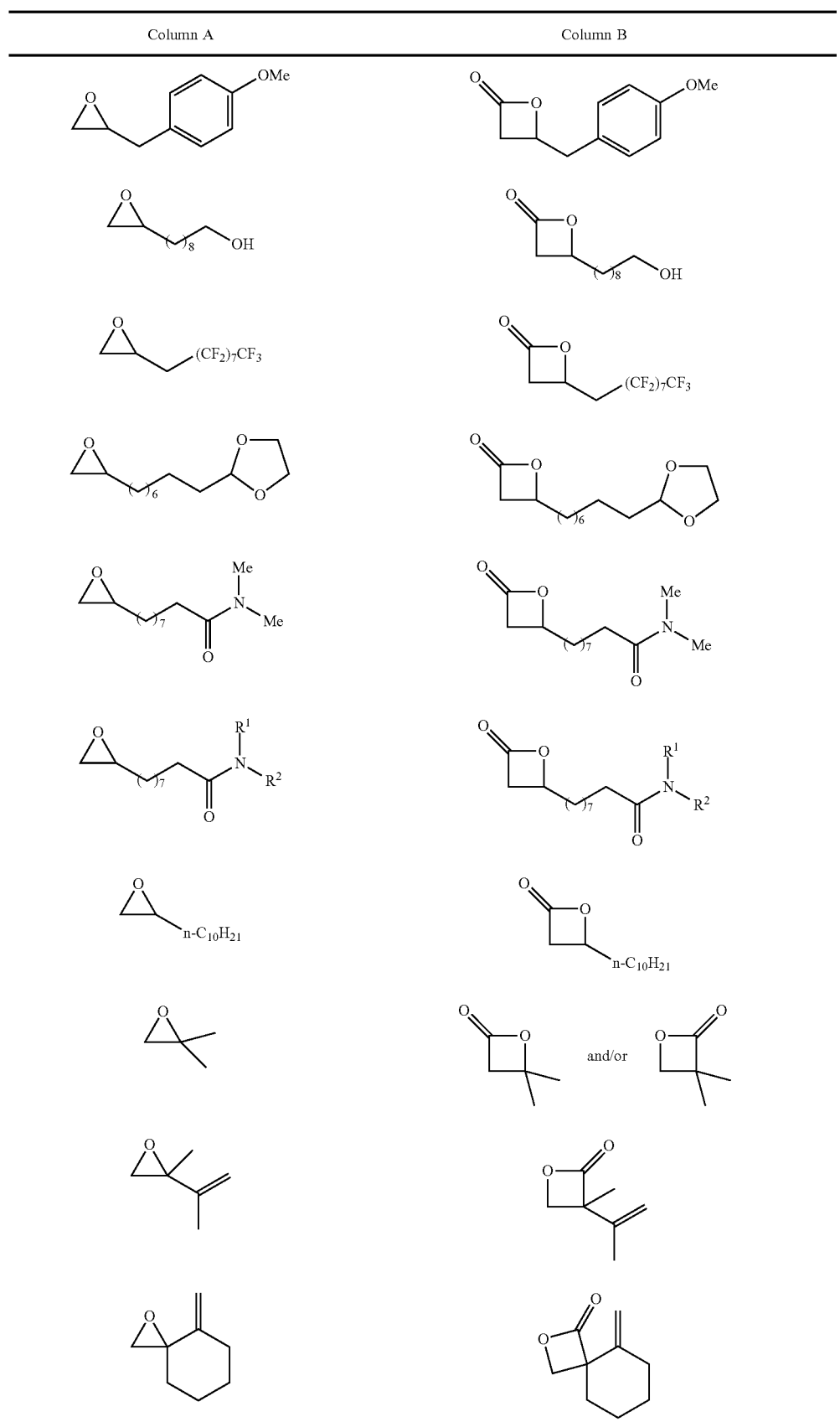

-continued
| Column A | Column B |
|---|---|
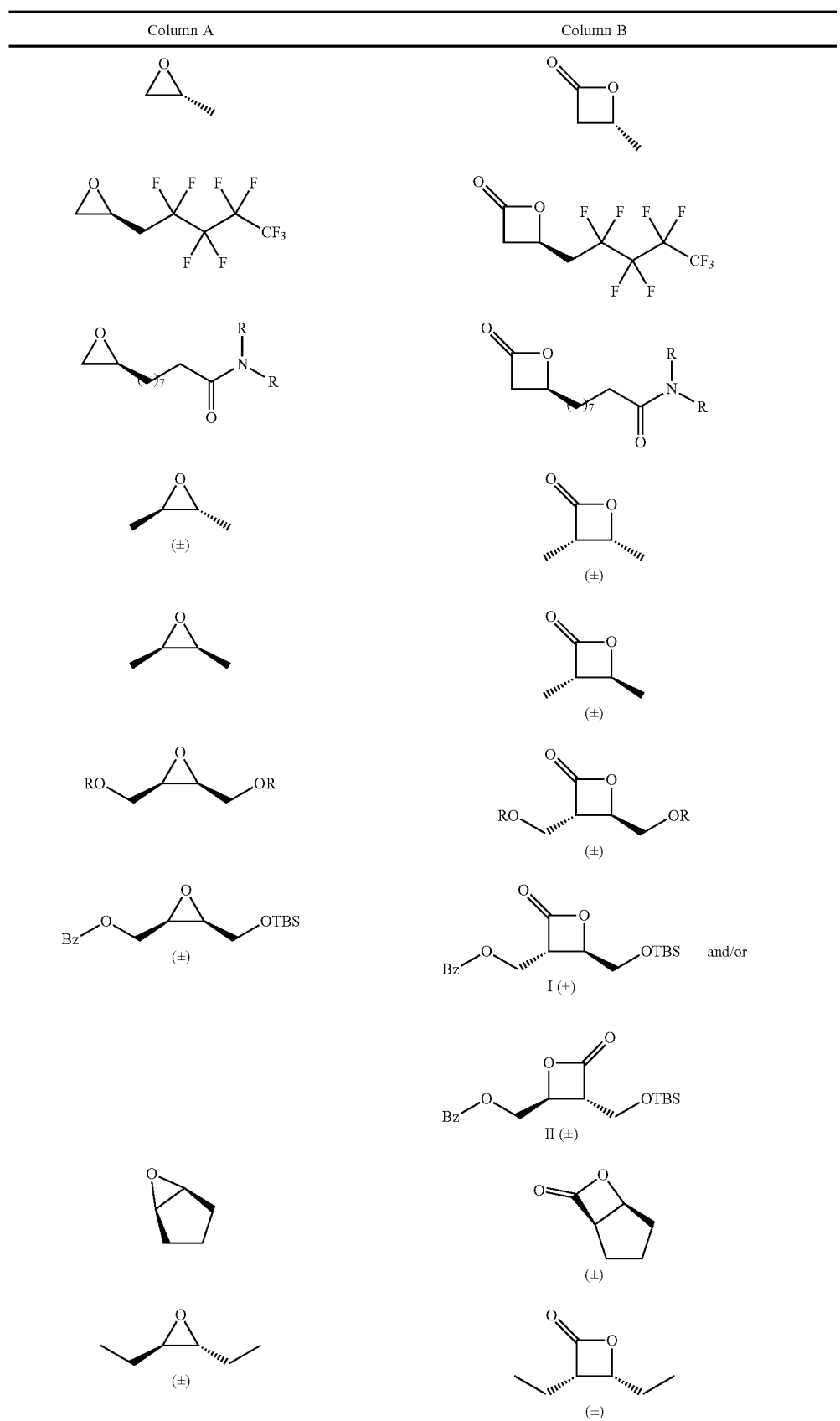

-continued
| Column A | Column B |
|---|---|
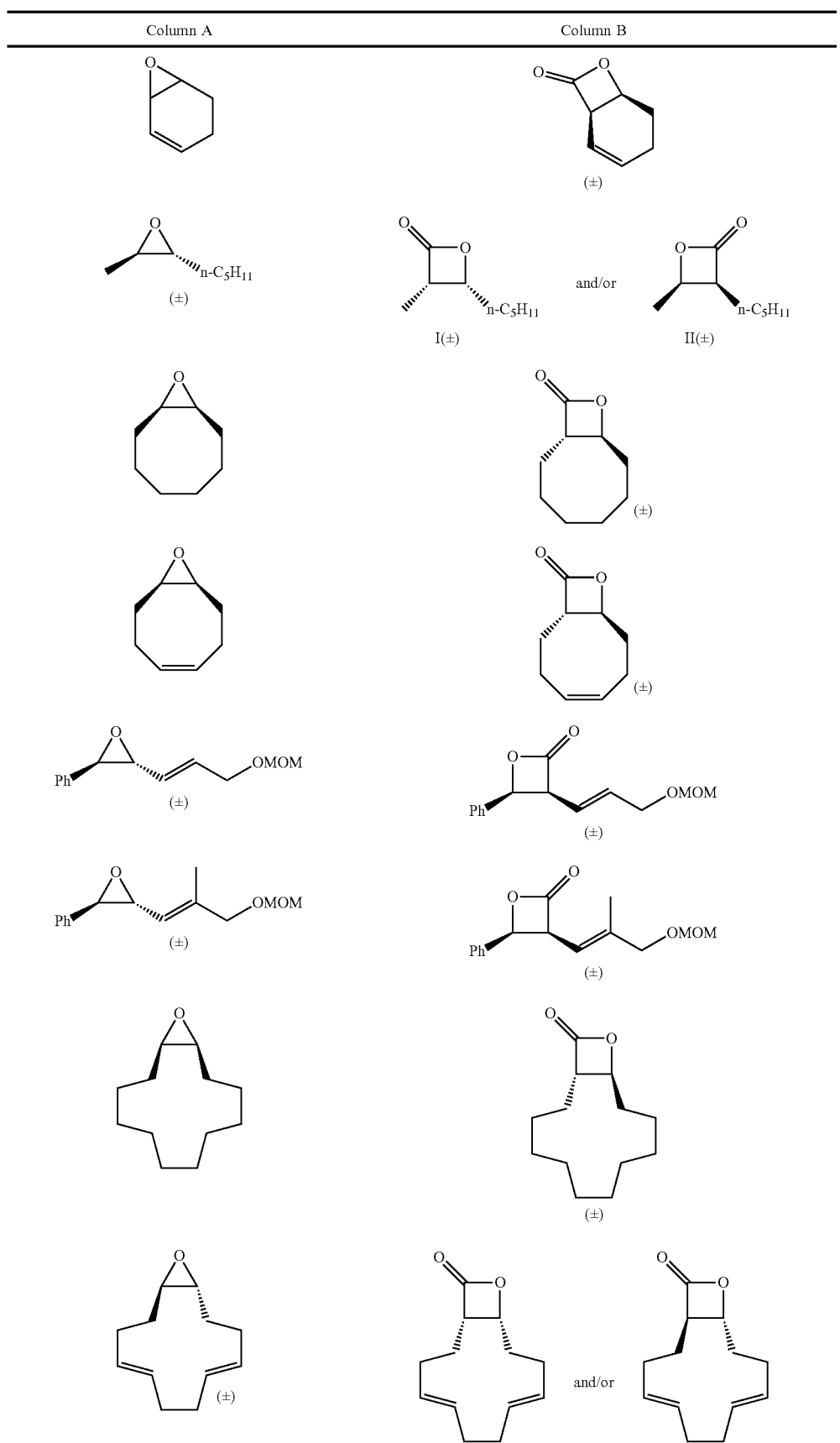

| Column A | Column B |
|---|---|

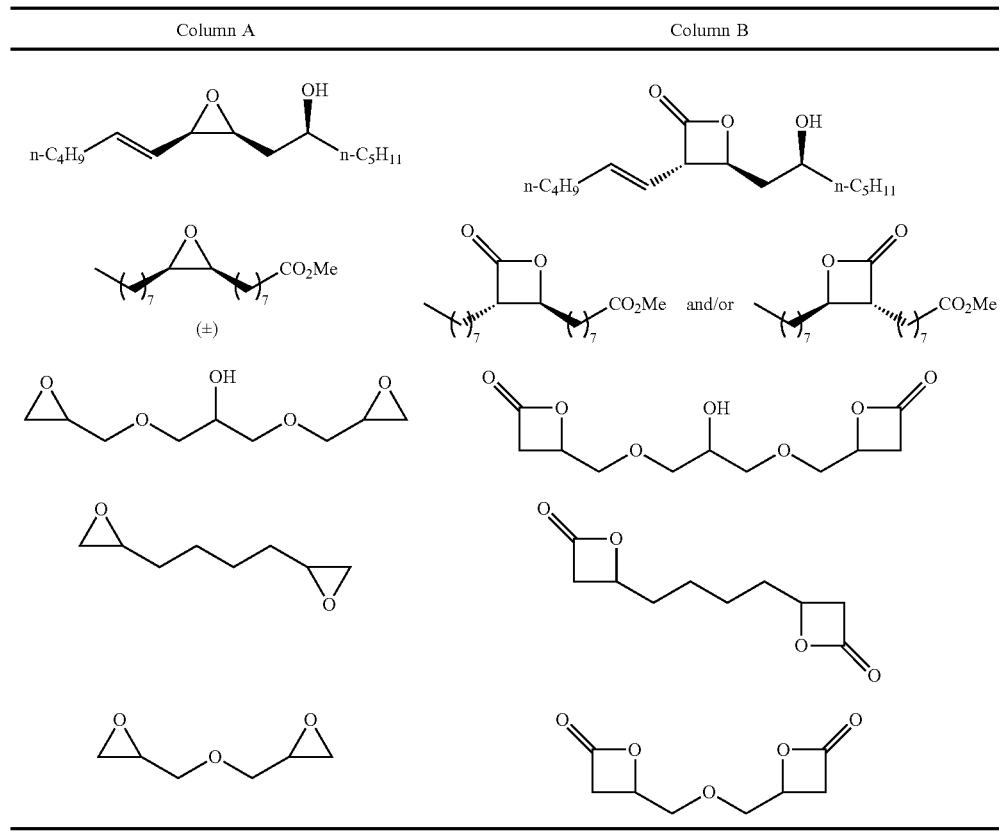

In certain preferred embodiments, the heterogenous catalyst includes a single metal carbonyl compound, but in certain other preferred embodiments, mixtures of two or more metal carbonyl compounds are provided. Thus, when a provided metal carbonyl compound "comprises", e.g., a neutral metal carbonyl compound, it is understood that the provided metal carbonyl compound can be a single metal carbonyl compound, or a metal carbonyl compound in combination with one or more metal carbonyl compounds. Preferably, the provided metal carbonyl compound is capable of ring-opening an epoxide and facilitating the insertion of carbon monoxide into the resulting metal carbon bond. Metal carbonyl compounds with this reactivity are well known in the art and are used for laboratory experimentation as well as in industrial processes such as hydroformylation.

In certain embodiments, metal carbonyl compounds include those described in U.S. Pat. No. 6,852,865. In other embodiments, the metal carbonyls may be those disclosed in U.S. patent application Ser. Nos. 10/820,958; and 10/586,826. In yet other embodiments, the metal carbonyls may be those disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In some embodiments, a provided metal carbonyl compound comprises an anionic metal carbonyl moiety. In other embodiments, a provided metal carbonyl compound comprises a neutral metal carbonyl compound. In some embodiments, a provided metal carbonyl compound comprises a metal carbonyl hydride or a hydrido metal carbonyl compound. In some embodiments, a provided metal carbonyl compound acts as a pre-catalyst which reacts in situ with one or more reaction components to provide an active species different from the compound initially provided. Such pre-catalysts are specifically encompassed as it is recognized that the active species in a given reaction may not be known with certainty; thus the identification of such a reactive species in situ does not itself depart from the spirit or teachings of the present disclosure.

In some embodiments, the metal carbonyl compound comprises an anionic metal carbonyl species. In some embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$, $[V(CO)_6]^-$

[Rh(CO)$_4$]$^-$, [Fe(CO)$_4$]$^{2-}$, [Ru(CO)$_4$]$^{2-}$, [Os(CO)$_4$]$^{2-}$, [Cr$_2$(CO)$_{10}$]$^{2-}$, [Fe$_2$(CO)$_8$]$^{2-}$, [Tc(CO)$_5$]$^-$, [Re(CO)$_5$]$^-$, and [Mn(CO)$_5$]$^-$. In some embodiments, the anionic metal carbonyl comprises [Co(CO)$_4$]$^-$. In some embodiments, a mixture of two or more anionic metal carbonyl complexes may be present in the heterogenous catalysts used in the methods.

The term "such as to provide a stable anionic metal carbonyl" for [Q$_d$M'$_e$(CO)$_w$]$^{y-}$ is used herein to mean that [Q$_d$M'$_e$(CO)$_w$]$^{y-}$ is a species characterizable by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for carbon monoxide to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments including an anionic metal carbonyl, one or more cations must also necessarily be present. In some variations, no particular constraints on the identity of such cations. In some embodiments, the cation associated with an anionic metal carbonyl compound comprises a reaction component of another category described herein. For example, in some embodiments, the metal carbonyl anion is associated with a cationic Lewis acid. In other embodiments, a cation associated with a provided anionic metal carbonyl compound is a simple metal cation such as those from Groups 1 or 2 of the periodic table (e.g., Na$^+$, Li$^+$, K$^+$, Mg$^{2+}$ and the like). In other embodiments, a cation associated with a provided anionic metal carbonyl compound is a bulky non electrophilic cation such as an 'onium salt' (e.g., Bu$_4$N$^+$, PPN$^+$, Ph$_4$P$^+$ Ph$_4$As$^+$, and the like). In other embodiments, a metal carbonyl anion is associated with a protonated nitrogen compound (e.g., a cation may comprise a compound such as MeTBD-H$^+$, DMAP-H$^+$, DABCO-H$^+$, DBU-H$^+$ and the like). In some embodiments, compounds comprising such protonated nitrogen compounds are provided as the reaction product between an acidic hydrido metal carbonyl compound and a basic nitrogen-containing compound (e.g., a mixture of DBU and HCo(CO)$_4$).

In some embodiments, a catalyst utilized in the methods described herein comprises a neutral metal carbonyl compound. In some embodiments, such neutral metal carbonyl compounds have the general formula Q$_d$M'$_e$(CO)$_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula QM'(CO)$_{w'}$. In some embodiments, the neutral metal carbonyl has the general formula M'(CO)$_{w'}$. In some embodiments, the neutral metal carbonyl has the general formula QM'$_2$(CO)$_{w'}$. In some embodiments, the neutral metal carbonyl has the general formula M'$_2$(CO)$_{w'}$. Suitable neutral metal carbonyl compounds include, but are not limited to: Ti(CO)$_7$; V$_2$(CO)$_{12}$; Cr(CO)$_6$; Mo(CO)$_6$; W(CO)$_6$ Mn$_2$(CO)$_{10}$, Tc$_2$(CO)$_{10}$, and Re$_2$(CO)$_{10}$ Fe(CO)$_5$, Ru(CO)$_5$ and Os(CO)$_5$ Ru$_3$(CO)$_{12}$, and Os$_3$(CO)$_{12}$ Fe$_3$(CO)$_{12}$ and Fe$_2$(CO)$_9$ Co$_4$(CO)$_{12}$, Rh$_4$(CO)$_{12}$, Rh$_6$(CO)$_{16}$, and Ir$_4$(CO)$_{12}$ Co$_2$(CO)$_8$ Ni(CO)$_4$.

The term "such as to provide a stable neutral metal carbonyl" for Q$_d$M'$_e$(CO)$_{w'}$ is used herein to mean that Q$_d$M'$_e$(CO)$_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for carbon monoxide to coordinate and therefore the value of w'. Typically, the stoichiometry of such compounds conforms to the "18-electron rule". Such knowledge is within the grasp of one having ordinary skill in the arts pertaining to the synthesis and characterization of metal carbonyl compounds.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the heterogenous catalyst utilized in the methods described above further includes a Lewis acidic component. In some embodiments, the heterogenous catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, where an included Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., R$_2$BX), a dihalo monoalkyl compound (e.g., RBX$_2$), an aryl halo boron compound (e.g., Ar$_2$BX or ArBX$_2$), or a trihalo boron compound (e.g., BCl$_3$ or BBr$_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where the heterogenous catalysts used in the processes described herein include a cationic metal complex, the metal complex has the formula $[(L^c)_v M_b]^{z+}$, where:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

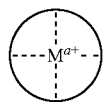

I wherein:

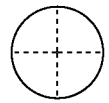

is a multidentate ligand;

M is a metal atom coordinated to the multidentate ligand;

a is the charge of the metal atom and ranges from 0 to 2; and

In some embodiments, provided metal complexes conform to structure II:

II

Where a is as defined above (each a may be the same or different), and $M^1$ is a first metal atom;

$M^2$ is a second metal atom;

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In some embodiments, the multidentate ligand is a salen derivative. In other embodiments, the multidentate ligand is a porphyrin derivative. In other embodiments, the multidentate ligand is a tetraphenylporphyrin derivative. In other embodiments, the multidentate ligand is a corrole derivative.

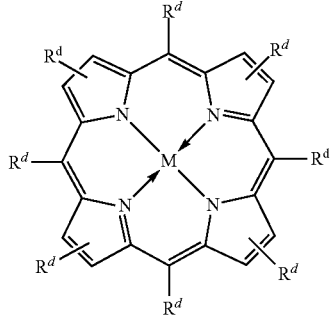

1

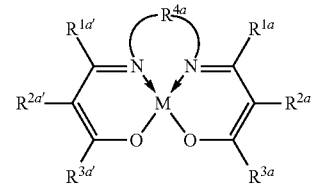

2

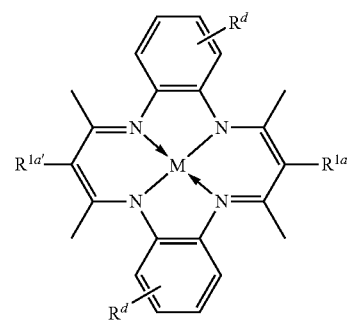

3

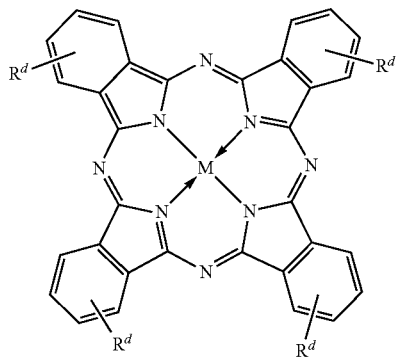

4

-continued

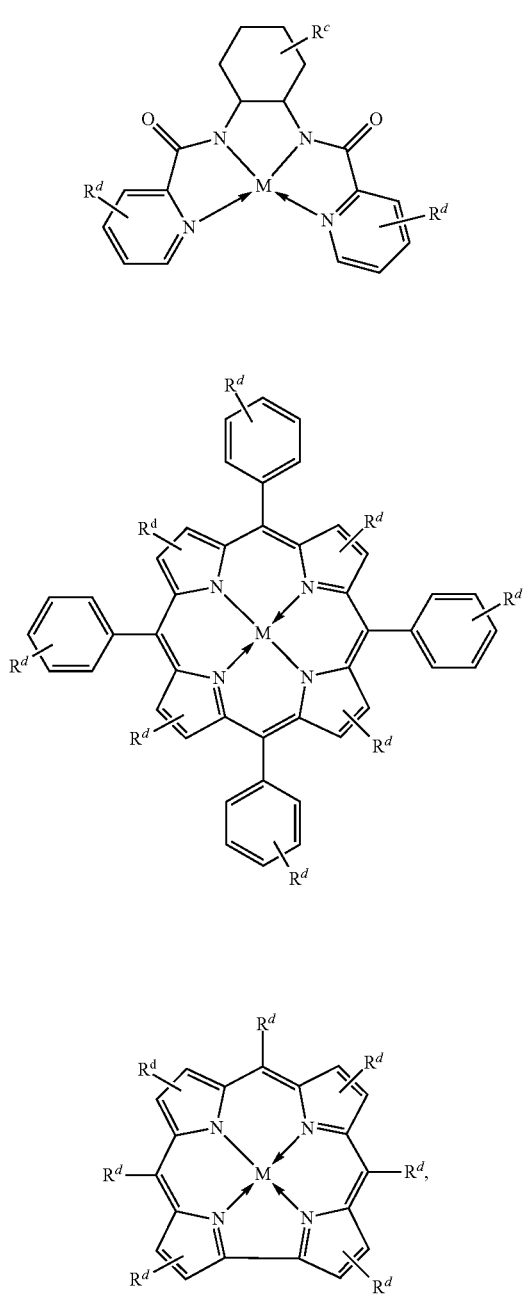

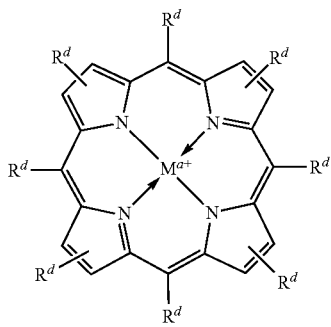

where each of $R^c$, $R^d$, $R^{1a}$, $R^{2a}$, $R^{3a}$, $R^{4a}$, $R^{1a'}$, $R^{2a'}$, $R^{3a'}$, and M, is as defined and described in the classes and subclasses herein.

In some embodiments, Lewis acids provided heterogenous catalysts used in systems and methods described herein comprise metal-porphinato complexes. In some embodiments, the moiety

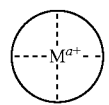

has the structure:

where each of M and a is as defined above and described in the classes and subclasses herein, and $R^d$ at each occurrence is independently hydrogen, halogen, $—OR^4$, $—NR^y_2$, $—SR^y$, $—CN$, $—NO_2$, $—SO_2R^y$, $—SOR^y$, $—SO_2NR^y_2$; $—CNO$, $—NR^ySO_2R^y$, $—NCO$, $—N_3$, $—SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or $R^y$.

In some embodiments, the moiety

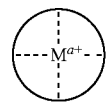

has the structure:

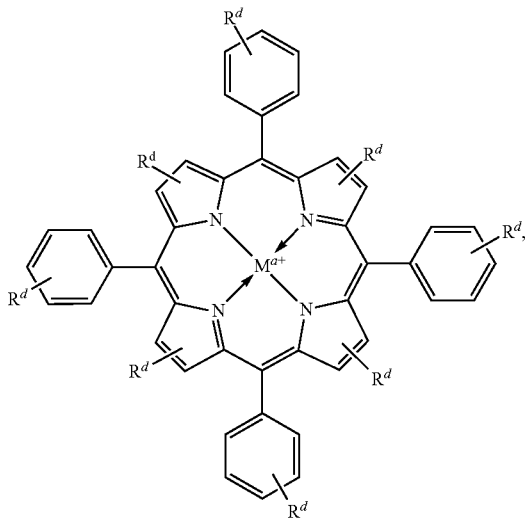

where M, a and $R^d$ are as defined above and in the classes and subclasses herein.

In some embodiments, the moiety

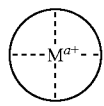

has the structure:

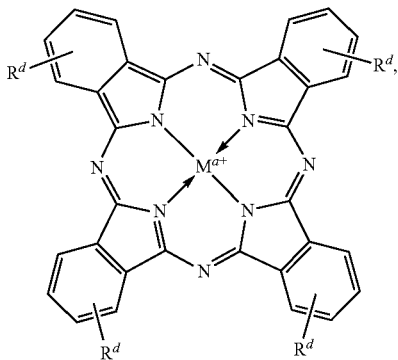

where M, a and $R^d$ are as defined above and in the classes and subclasses herein.

In some embodiments, Lewis acids included in heterogenous catalysts used in the processes described herein comprise metallo salenate complexes. In some embodiments, the moiety

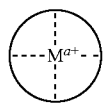

has the structure:

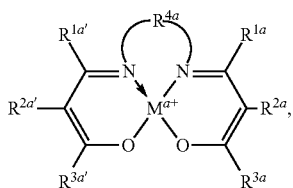

wherein:

M, and a are as defined above and in the classes and subclasses herein.

$R^{1a}$, $R^{1a'}$, $R^{2a}$, $R^{2a'}$, $R^{3a}$, and $R^{3a'}$ are independently hydrogen, halogen, $-OR^4$, $-NR^y_2$, $-SR^y$, $-CN$, $-NO_2$, $-SO_2R^y$, $-SOR^y$, $-SO_2NR^y_2$; $-CNO$, $-NR^ySO_2R^y$, $-NCO$, $-N_3$, $-SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and $R^{4a}$ is selected from the group consisting of:

e)

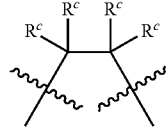

f)

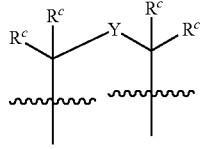

g)

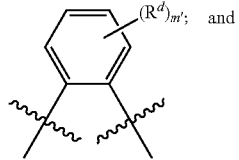
and h)

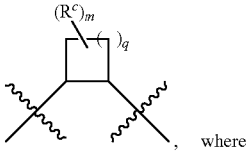

, where $R^c$ at each occurrence is independently hydrogen, halogen, $-OR^4$, $-NR^y_2$, $-SR^y$, $-CN$, $-NO_2$, $-SO_2R^y$, $-SOR^y$, $-SO_2NR^y_2$; $-CNO$, $-NR^ySO_2R^y$, $-NCO$, $-N_3$, $-SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:

two or more $R^c$ groups may be taken together with the carbon atoms to which they are attached and any intervening atoms to form one or more rings;

when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

where $R^4$ and $R^y$ are as defined above and in classes and subclasses herein;

Y is a divalent linker selected from the group consisting of: —$NR^y$—, —$N(R^y)C(O)$—, —$C(O)NR^y$—, —O—, —C(O)—, —OC(O)—, —C(O)O—, —S—, —SO—, —$SO_2$—, —C(=S)—, —C(=$NR^y$)—, —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive;

q is 0 or an integer from 1 to 4, inclusive; and x is 0, 1, or 2.

In some embodiments, a provided Lewis acid comprises a metallo salen compound, as shown in formula Ia:

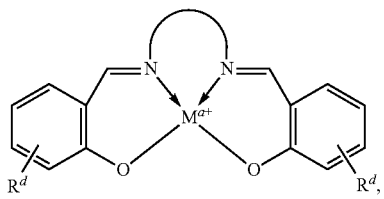

Ia wherein each of M, $R^d$, and a, is as defined above and in the classes and subclasses herein,

represents is an optionally substituted moiety linking the two nitrogen atoms of the diamine portion of the salen ligand, where

is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —OC(O)O—, —O—, —C(O)—, —OC(O)—, —C(O)O—, —S—, —SO—, —$SO_2$—, —C(=S)—, —C(=$NR^y$)—, —C(=$NOR^y$)— or —N=N—.

In some embodiments metal complexes having formula Ia above, at least one of the phenyl rings comprising the salicylaldehyde-derived portion of the metal complex is independently selected from the group consisting of:

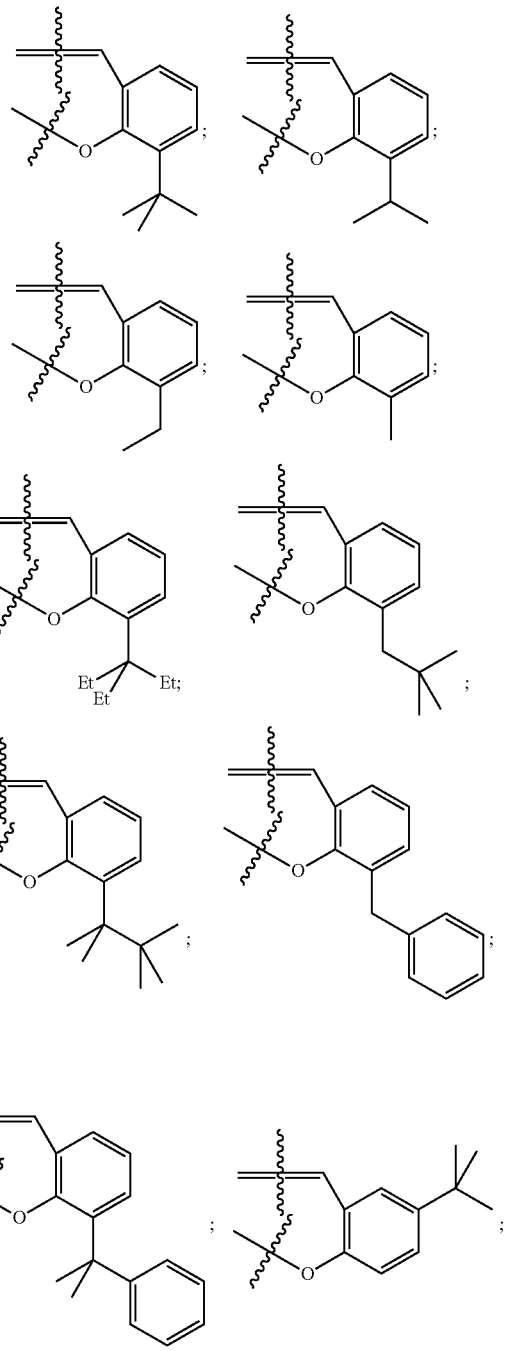

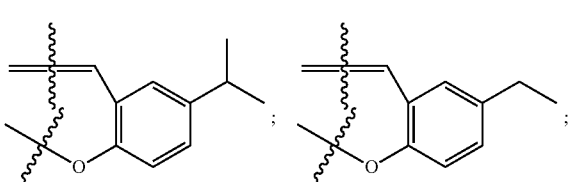

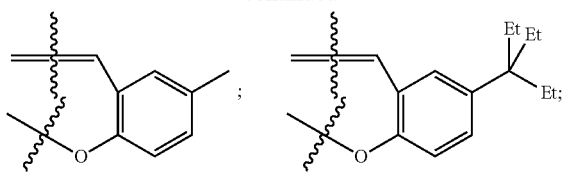
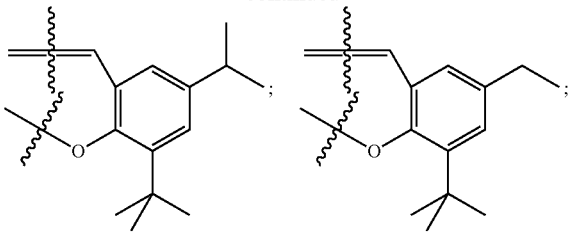
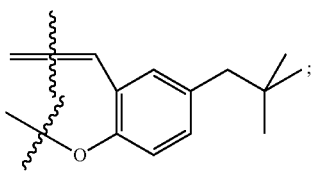
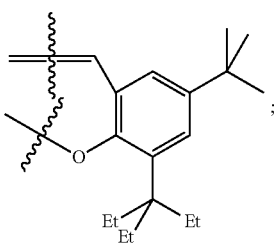
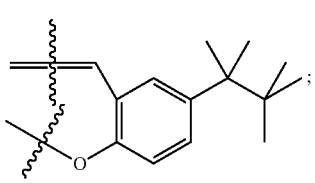
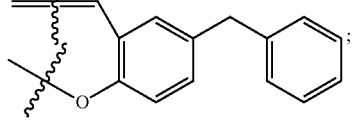
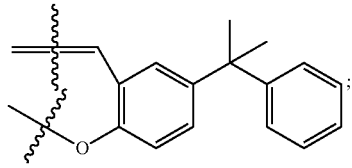
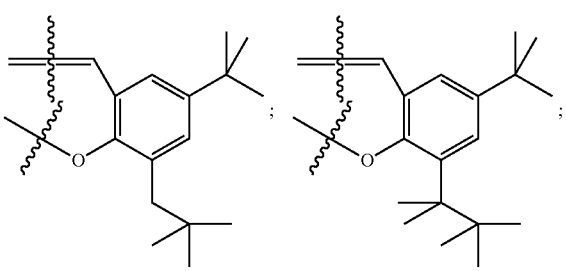
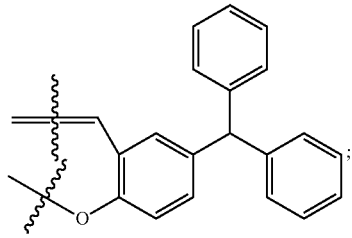
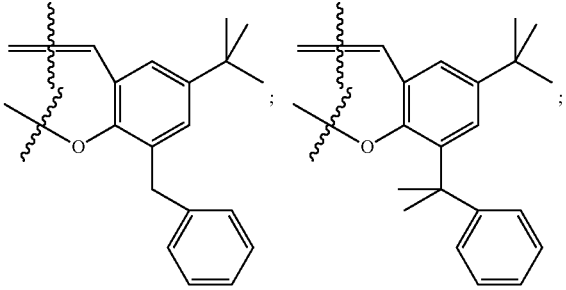
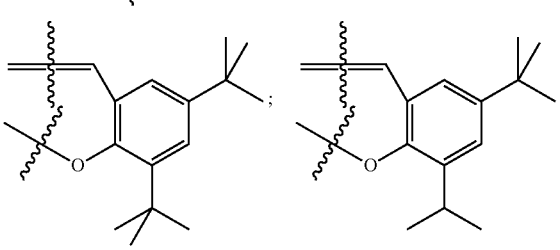
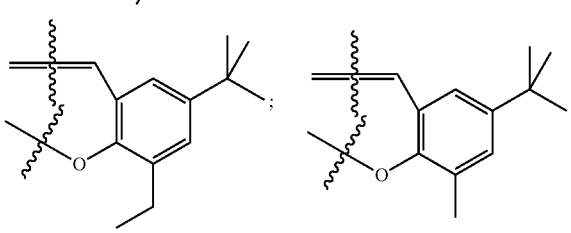
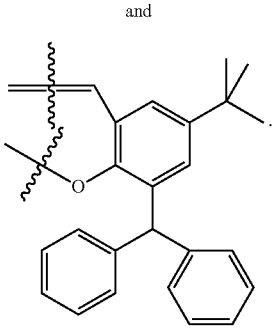
and
In some embodiments, a provided Lewis acid comprises a metallo salen compound, conforming to one of formulae Va or Vb:

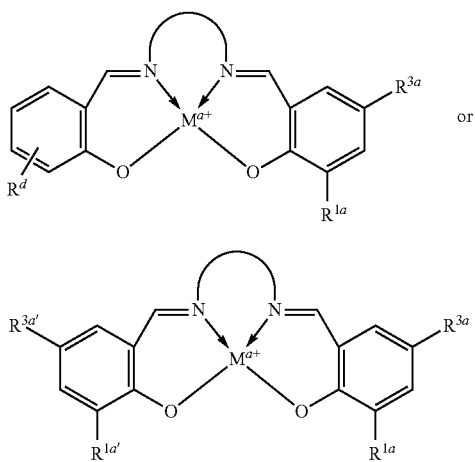

where M, a, $R^d$, $R^{1a}$, $R^{1a}$, $R^{1a'}$, $R^{3a'}$, and

are as defined above and in the classes and subclasses herein.

In some embodiments of metal complexes having formulae Va or Vb, each $R^{1a}$ and $R^{3a}$ is, independently, optionally substituted $C_1$-$C_{20}$) aliphatic.

In some embodiments, the moiety

comprises an optionally substituted 1,2-phenyl moiety.

In some embodiments, Lewis acids included in heterogenous catalysts used in processes described herein comprise metal—tmtaa complexes. In some embodiments, the moiety

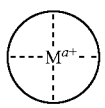

has the structure:

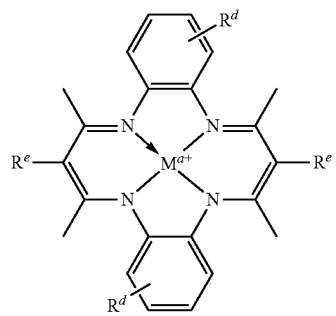

where M, a and $R^d$ are as defined above and in the classes and subclasses herein, and $R^e$ at each occurrence is independently hydrogen, halogen, —OR, —NR$^y_2$, —SR$^y$, —CN, —NO$_2$, —SO$_2$R$^y$, —SOR$^y$, —SO$_2$NR$^y_2$; —CNO, —NR$^y$SO$_2$R$^y$, —NCO, —N$_3$, —SiR$^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

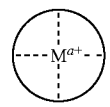

has the structure:

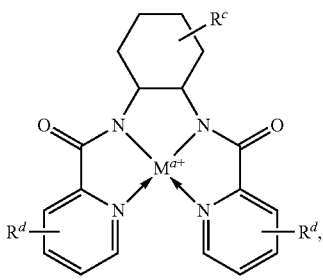

where each of M, a, $R^c$ and $R^d$ is as defined above and in the classes and subclasses herein.

In some embodiments, where heterogenous catalysts used in systems and methods described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ has an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the heterogenous catalyst includes a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand. In some embodiments, the tetradentate ligand may be bound to siliceous material and/or tethered to the siliceous material by one or more other molecules.

In some embodiments, the heterogenous catalyst includes a carbonyl cobaltate in combination with an aluminum porphyrin compound. In some embodiments, the heterogenous catalyst is $[(TPP)Al(THF)_2][Co(CO)_4]$ where TPP stands for tetraphenylporphyrin and THF stands for tetrahydrofuran.

In certain preferred embodiments, the heterogenous catalyst includes a carbonyl cobaltate in combination with a chromium porphyrin compound.

In some embodiments, the heterogenous catalyst includes a carbonyl cobaltate in combination with a chromium salen compound. In some embodiments, the heterogenous catalyst includes a carbonyl cobaltate in combination with a chromium salophen compound.

In some embodiments, the heterogenous catalyst includes a carbonyl cobaltate in combination with a metal salen compound. In certain embodiments, the metal salen compound is an aluminum salen compound. In some embodiments, the heterogenous catalyst includes a carbonyl cobaltate in combination with a metal salophen compound. In certain embodiments, the metal salophen compound is an aluminum salophen compound.

In some embodiments, one or more neutral two electron donors coordinate to M, $M^1$ or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

In certain embodiments, the heterogenous catalyst includes a carbonyl cobaltate in combination with an aluminum porphyrin compound and a solid support. In certain embodiments, the heterogenous catalyst includes a carbonyl cobaltate in combination with a chromium porphyrin compound and a solid support. In certain embodiments, the heterogenous catalyst includes a carbonyl cobaltate in combination with a chromium salen compound and a solid support. In certain embodiments, the heterogenous catalyst includes a carbonyl cobaltate in combination with a chromium salophen compound and a solid support. In certain embodiments, the heterogenous catalyst includes a carbonyl cobaltate in combination with an aluminum salen compound and a solid support. In certain embodiments, the heterogenous catalyst includes a carbonyl cobaltate in combination with an aluminum salophen compound and a solid support.

In certain preferred embodiments, the heterogenous catalyst of the present invention includes a solid support such as a structured zeolite. In certain embodiments, the heterogenous catalyst includes a cationic Lewis acid functional group and/or an anionic metal carbonyl supported by a structured zeolite. In a further embodiment, the structured zeolite has a faujasite, mordenite, or ZSM-5 (MFI) structure. In a further embodiment, the structure has the hexagonal pore arrangement of MCM-41. In a further embodiment, the structure has the cubic pore arrangement of MCM-48. In a further embodiment, the structure has the lamellar pore arrangement of MCM-50. In a further embodiment, the structure has pores organized in a foam arrangement. In a further embodiment, the structure has randomly placed pores. In a further embodiment, the structured zeolite material is Y[MCM-41], MOR[MCM-41], or ZSM-5[MCM-41]. In a further embodiment, the mean pore diameter within the structure is about 2 to about 5 nm. In a further embodiment, the mean pore diameter within the structure is about 2 to about 3 nm. In a further embodiment, the wall thickness within the structure is about 1 to about 5 nm. In a further embodiment, the wall thickness within the structure is about 1 to about 3 nm.

The synthesis of fully crystalline structured zeolites is applicable to a wide variety of materials. The first strategy is based on the short-range reorganization of a zeolite structure in the presence of a surfactant to accommodate mesoporosity without loss of zeolitic full crystallinity. A zeolite is added to a pH controlled solution containing a surfactant. Alternatively, a zeolite is added to a pH controlled solution and thereafter a surfactant is added. The pH controlled solution can be, for example, a basic solution with a pH ranging from about 8 to about 12, or from about 9 to about 11, or alternatively, the basic solution pH can be about 10. The strength of the base and the concentration of the basic solution are selected to provide a pH within the desired range. Any suitable base can be employed that falls within the desired pH range.

A charged chemical species, for example a positively charged chemical species, can be anchored to the fully crystalline structure. The charged chemical species can be cations of an element, quaternary amines, ammonium ions, pyridinium ions, or phosphonium ions, or any combination thereof. Alternatively, a chemical species can be anchored and/or covalently bonded to the fully crystalline structure. The chemical species can be a basic chemical species, an inorganic base, an organic base, hydroxide, amine, pyridine, or phosphine, or any combination thereof.

In certain embodiments, the heterogenous catalyst includes a solid support that comprises a siliceous based material, e.g., silica, and/or a carbon based material, e.g., carbon black or activated carbon, although any of a variety of other suitable supporting materials may be used. In some embodiments, the heterogenous catalyst may comprise a material selected from the group comprising silica, alumina, titania, silica/alumina, pyrogenic silica, high purity silica, zirconia, carbon (e.g., carbon black or activated carbon), zeolites and mixtures thereof. In some embodiments, the heterogenous catalyst comprises a siliceous material such as silica, pyrogenic silica, or high purity silica. In some embodiments, the siliceous material is substantially free of alkaline earth metals, such as magnesium and calcium.

In certain preferred embodiments, the heterogeneous catalyst comprises a cationic Lewis acid functional group and/or an anionic metal carbonyl supported on a heterogenous solid support formed by contacting the support material and the cationic Lewis acid functional group and/or the anionic metal carbonyl by a method such as physical mixture, dry impregnation, wet impregnation, incipient wet impregnation, ion-exchange, and vaporization.

In some embodiments, at least one metal complex may be impregnated into a heterogenous solid support. With impregnation, the at least one metal complex and heterogenous solid support material are mixed together followed by drying and calcination to form the heterogenous catalyst. With simultaneous impregnation, it may be desired to employ a dispersion agent, surfactant, or solubilizing agent, e.g., ammonium oxalate or an acid such as acetic or nitric acid, to facilitate the dispersing or solubilizing of the first, second and/or optional third metal complex in the event one or more of the metal complexes are incompatible.

In certain embodiments, sequential impregnation may be used to form the heterogenous catalyst. With sequential impregnation, a first metal complex may be first added to a heterogenous solid support material followed by drying and calcining, and the resulting material may then be impregnated by subsequent one or more metal complex followed by an additional drying and calcining to form the final heterogenous catalyst. In some embodiments, additional metal complexes may be added either with the first and/or second metal complex or in a separate sequential impregnation, followed by drying and calcination. In some embodiments, combinations of sequential and simultaneous impregnation may be employed if desired.

The embodiments described herein are not intended to be limited to the aspects shown, but are to be accorded the widest scope consistent with the principles and features disclosed herein.

What is claimed is:

1. A process for producing a beta-lactone product from a carbon monoxide reagent and an epoxide reagent, the process comprising:
   a. passing the epoxide reagent to a reaction zone;
   b. passing the carbon monoxide reagent to the reaction zone;
   c. contacting the epoxide reagent and the carbon monoxide reagent with a heterogenous catalyst at reaction conditions in the reaction zone to produce the beta-lactone product; and
   d. removing the beta-lactone product from the reaction zone;
   wherein at least one of the epoxide reagent and the carbon monoxide reagent is derived from renewable sources; and
   wherein the heterogenous catalyst comprises:
      a solid support comprising at least one zeolite having a faujasite structure, a mordenite structure, a ZSM-5 (MFI) structure, a hexagonal pore arrangement of MCM-41, a cubic pore arrangement of MCM-48, or a lamellar pore arrangement of MCM-50,
      a cationic Lewis acid functional group, and
      a metal carbonyl compound comprising at least one anionic metal carbonyl compound or neutral metal carbonyl compound.

2. The process of claim 1, wherein the epoxide reagent comprises ethylene oxide, propylene oxide, 1,2-epoxyhexane, 1,2-epoxydodecane, 3,4-epoxy-1-butene, 1,2-epoxy-5-hexene, 1,2-epoxy-9-decene, isoprene monoxide, epichlorohydrin, 1,3-butadiene diepoxide, 1,2,7,8-diepoxyoctane, 1,2-epoxycyclopentane, or cyclooctene oxide.

3. The process of claim 1, wherein the metal carbonyl compound is a metal porphyrin compound, a metal salen compound, a metal salophen compound.

4. The process of claim 1, wherein the reaction zone includes at least one of a fixed bed reactor, a moving bed reactor, a fluidized bed reactor, a trickle bed reactor, a catalytic distillation zone, a continuously stirred tank reactor, or a tubular reactor.

5. The process of claim 1, wherein the reaction conditions include a pressure of from atmospheric pressure to 600 psi, at a weight hourly space velocity of 0.25 to 20 $hr^{-1}$.

6. The process of claim 1, wherein the concentration of the epoxide reagent in the reaction zone is equal to or up to 10% higher than the stoichiometric value for a carbonylation reaction.

7. The process of claim 1, wherein the reaction zone receives a Lewis base additive selected from the group consisting of a modified THF, 2,6-lutidine, imidazole, 1-methylimidazole 4-dimethylaminopyridine, trihexylamine, and triphenylphosphine.

8. The process of claim 1, wherein the heterogenous catalyst comprises an anionic metal carbonyl species having a general formula of $[Q_d M'_e(CO)_w]^{y-}$, wherein:
   Q is a ligand, provided that d is not 0,
   M' is a metal atom,
   d is an integer between 0 and 8 inclusive,
   e is an integer between 1 and 6 inclusive,
   w is the number needed to provide the stable anionic metal carbonyl complex,
   y is the charge of the anionic metal carbonyl species, and
   the anionic metal carbonyl species is bound to a solid support comprising silica, alumina, titania, zirconia, carbon black, activated carbon, or zeolite, or any combination thereof.

9. The process of claim 8, wherein the anionic metal carbonyl species comprises at least one of $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$.

10. The process of claim 1, wherein the cationic Lewis acid functional group comprises Zn(II), Cu(II), Mn(II), Co(II), Ru(II), Fe(II), Rh(II), Ni(II), Pd(II), Mg(II), Al(III), Cr(III), Fe(III), Co(III), Ti(III) In(III), Ga(III), Mn(III), Ti(IV), or Cr(IV).

11. A process for producing a beta-lactone product from a carbon monoxide reagent and an epoxide reagent, the process comprising:
   a. passing the epoxide reagent to a reaction zone;
   b. passing the carbon monoxide reagent to the reaction zone;
   c. contacting the epoxide reagent and the carbon monoxide reagent with heterogenous catalyst at reaction conditions in the reaction zone to produce the beta-lactone product, wherein the heterogenous catalyst comprises a solid support, a cationic Lewis acid functional group and a metal carbonyl compound comprising at least one anionic metal carbonyl compound or neutral metal carbonyl compound; and d. removing the beta-lactone product from the reaction zone;

wherein at least one metal complex is impregnated into a solid support comprising a crystalline structure by mixing the metal complex with the crystalline structure followed by drying and calcination to form the heterogenous catalyst.

12. The process of claim 11, wherein a first metal complex is mixed with the crystalline structure followed by drying and calcining to produce an impregnated solid support and the impregnated solid support is mixed with an additional metal complex followed by an additional drying and calcining to form the heterogenous catalyst.

13. The process of claim 11, wherein the cationic Lewis acid functional group is a cationic metal complex having the general formula $[(L^c)_v M_b]^{z+}$, wherein:

$L^c$ is at least one ligand;

M is at least one metal atom;

v is an integer from 1 to 4 inclusive;

b is an integer from 1 to 2 inclusive; and z is an integer greater than 0 that represents the cationic charge on the metal complex.

14. The process of claim 13, wherein $L^c$ is at least one porphyrin ligand, salen ligand, dibenzotetramethyltetraaza [14]annulene (tmtaa) ligand, phthalocyaninate ligand, Trost ligand, tetraphenylporphyrin ligand, or corrole ligand.

15. The process of claim 11, wherein the metal carbonyl compound comprises a phosphine ligand, an amine ligand, a cyclopentadienyl ligand, a heterocyclic ligand, nitrile, or phenol, or any combination thereof.

16. The process of claim 1, wherein the epoxide reagent is ethylene oxide, and the beta-lactone product is beta-propiolactone.

17. The process of claim 11, wherein the epoxide reagent is ethylene oxide, and the beta-lactone product is beta-propiolactone.

18. The process of claim 8, wherein the solid support comprises silica/alumina, pyrogenic silica, or high purity silica, or any combination thereof.

19. The process of claim 13, wherein M comprises Zn, Cu, Mn, Ru, Fe, Co, Rh, Ni, Pd, Mg, Al, Cr, Ti, In, or Ga, or any combination thereof.

* * * * *